US010850071B2

(12) United States Patent
Appling et al.

(10) Patent No.: US 10,850,071 B2
(45) Date of Patent: Dec. 1, 2020

(54) EXPANDABLE INTRODUCER ASSEMBLY AND METHOD OF USING SAME

(71) Applicant: Freudenberg Medical, LLC, Carpinteria, CA (US)

(72) Inventors: Anthony Appling, Crestwood, KY (US); Simon Furnish, Louisville, KY (US); Ben Morris, Jeffersonville, IN (US); Cody Wetzel, New Salisbury, IN (US); Timothy S. Zeis, Charlestown, IN (US)

(73) Assignee: FREUDENBERG MEDICAL, LLC, Carpinteria, CA (US)

( * ) Notice: Subject to any disclaimer, the term of this patent is extended or adjusted under 35 U.S.C. 154(b) by 638 days.

(21) Appl. No.: 15/337,835

(22) Filed: Oct. 28, 2016

(65) Prior Publication Data

US 2018/0117284 A1    May 3, 2018

(51) Int. Cl.
*A61M 25/06* (2006.01)
*A61M 39/06* (2006.01)
(Continued)

(52) U.S. Cl.
CPC .... *A61M 25/0662* (2013.01); *A61M 25/0097* (2013.01); *A61M 25/09* (2013.01);
(Continued)

(58) Field of Classification Search
CPC .... A61M 29/02; A61M 3/0291; A61M 25/04; A61M 25/10; A61M 2029/025;
(Continued)

(56) References Cited

U.S. PATENT DOCUMENTS

| 4,921,479 A | 5/1990 | Grayzel |
| 5,203,780 A | 4/1993 | Liebler |
(Continued)

OTHER PUBLICATIONS

EP Search Report; Appl No. 19206088.7; dated Apr. 17, 2020; 9 pages.

*Primary Examiner* — Brandy S Lee
*Assistant Examiner* — Nidah M Hussain
(74) *Attorney, Agent, or Firm* — Dickinson Wright PLLC

(57) ABSTRACT

An expandable introducer assembly includes a dilator subassembly extending from a proximal end to a distal end. The dilator subassembly includes a dilator having an insertion portion disposed adjacent the distal end, an expansion portion disposed adjacent the distal end, and a tapered transition portion disposed between the insertion and expansion portions. The dilator subassembly includes a distal sheath disposed in overlaying relationship with the insertion portion of the dilator. An introducer subassembly is disposed in coaxial relationship with the expansion portion of the dilator, and includes a valve disposed adjacent the proximal end and an introducer sheath extending from the valve in overlaying relationship with the expansion portion of the dilator. An expandable sheath subassembly is releasably interlocked with the dilator subassembly and includes an expandable sheath disposed in overlaying relationship with the tapered transition portion and in nested relationship between the insertion portion and the distal sheath.

20 Claims, 12 Drawing Sheets

(51) Int. Cl.
*A61M 25/00* (2006.01)
*A61M 25/09* (2006.01)

(52) U.S. Cl.
CPC ..... *A61M 39/06* (2013.01); *A61M 2025/0687* (2013.01); *A61M 2039/0633* (2013.01)

(58) Field of Classification Search
CPC ..... A61M 25/0662; A61M 25/01; A61F 2/95; A61F 2/962; A61B 17/3439; A61B 17/3423
USPC ....................................................... 604/507
See application file for complete search history.

(56) References Cited

U.S. PATENT DOCUMENTS

| | | | |
|---|---|---|---|
| 5,256,150 | A | 10/1993 | Quiachon et al. |
| 5,447,503 | A | 9/1995 | Miller |
| 5,935,122 | A * | 8/1999 | Fourkas ............... A61M 25/005 604/249 |
| 5,997,508 | A | 12/1999 | Lunn et al. |
| 6,183,443 | B1 | 2/2001 | Kratoska et al. |
| 6,443,979 | B1 | 9/2002 | Stalker et al. |
| 2002/0007152 | A1 | 1/2002 | Hermann et al. |
| 2005/0085841 | A1 | 4/2005 | Eversull et al. |
| 2007/0255305 | A1 | 11/2007 | McMichael et al. |
| 2008/0167606 | A1 | 7/2008 | Dann et al. |
| 2010/0030162 | A1 | 2/2010 | Cremascoli et al. |
| 2010/0094392 | A1 | 4/2010 | Nguyen et al. |
| 2011/0112567 | A1 | 5/2011 | Lenker et al. |
| 2014/0025036 | A1 | 1/2014 | Bierman et al. |
| 2016/0067454 | A1 * | 3/2016 | Furnish ................. A61M 39/06 606/108 |
| 2016/0128723 | A1 | 5/2016 | Ginn et al. |
| 2017/0232236 | A1 | 8/2017 | Al-Rashdan et al. |

* cited by examiner

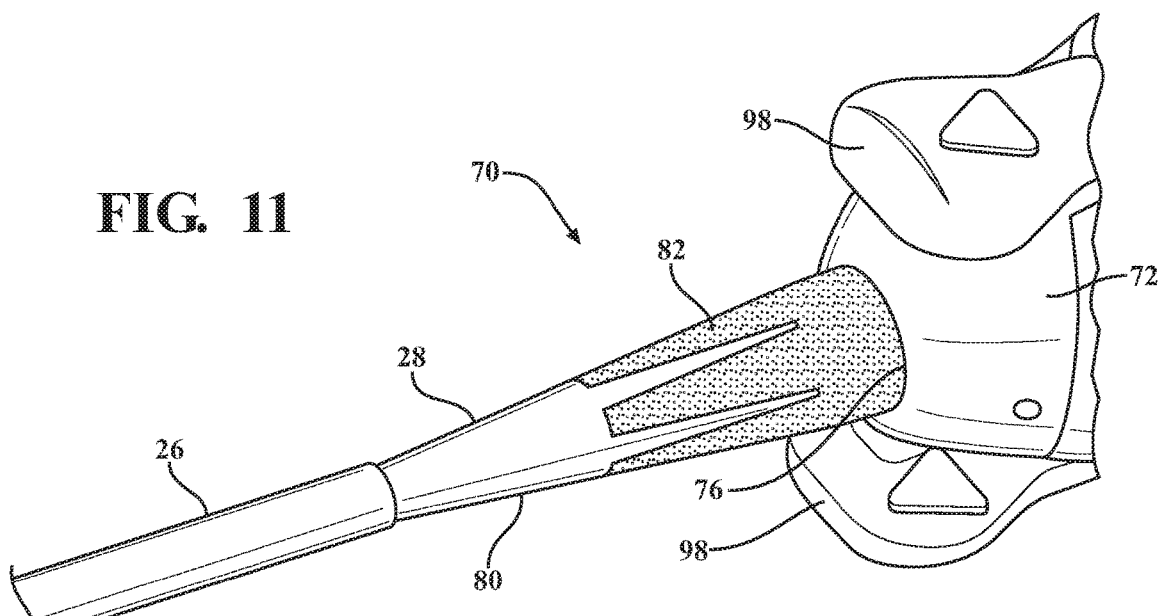
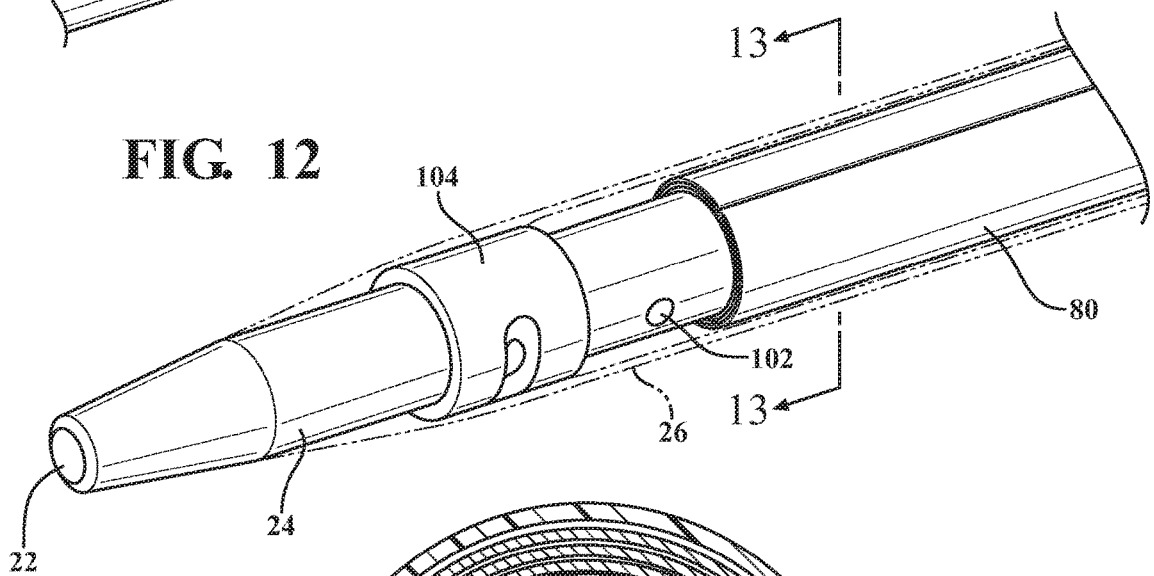
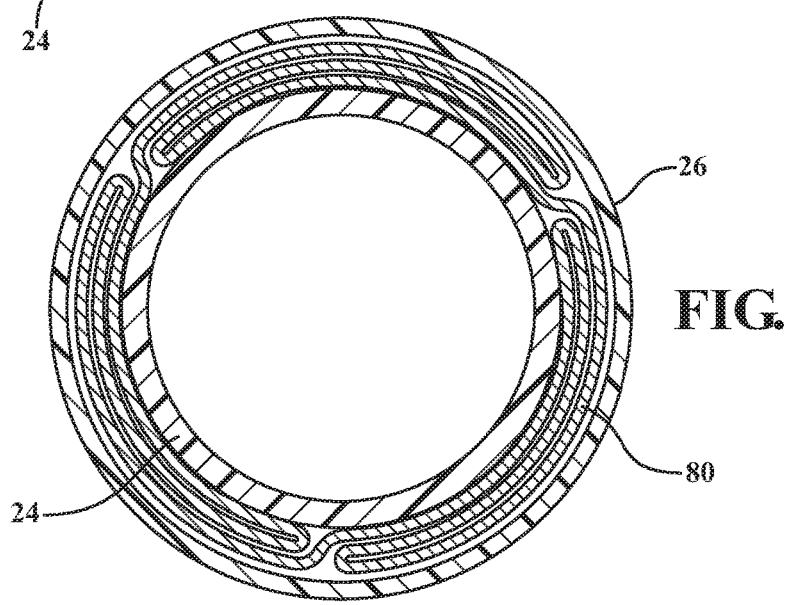

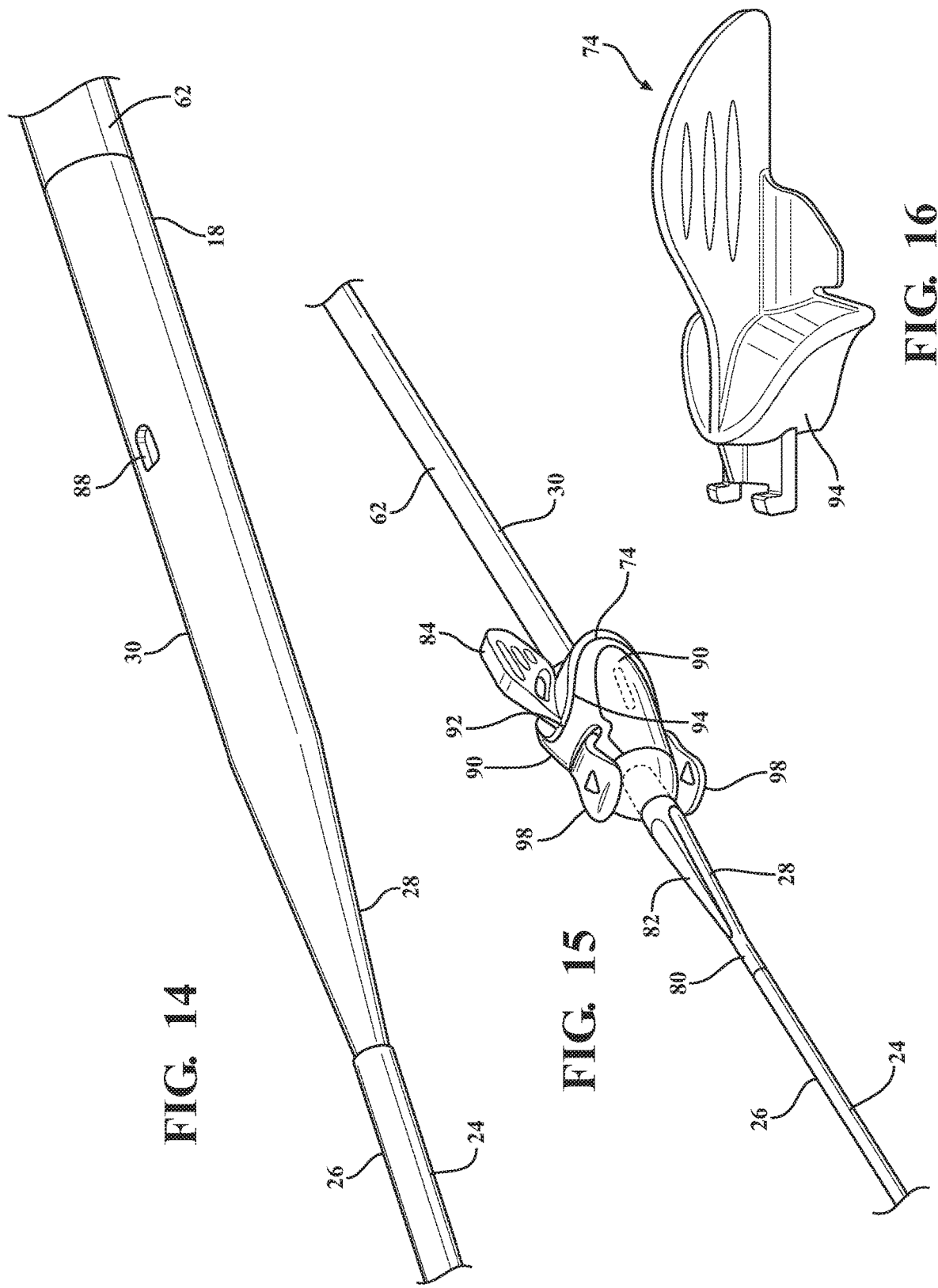

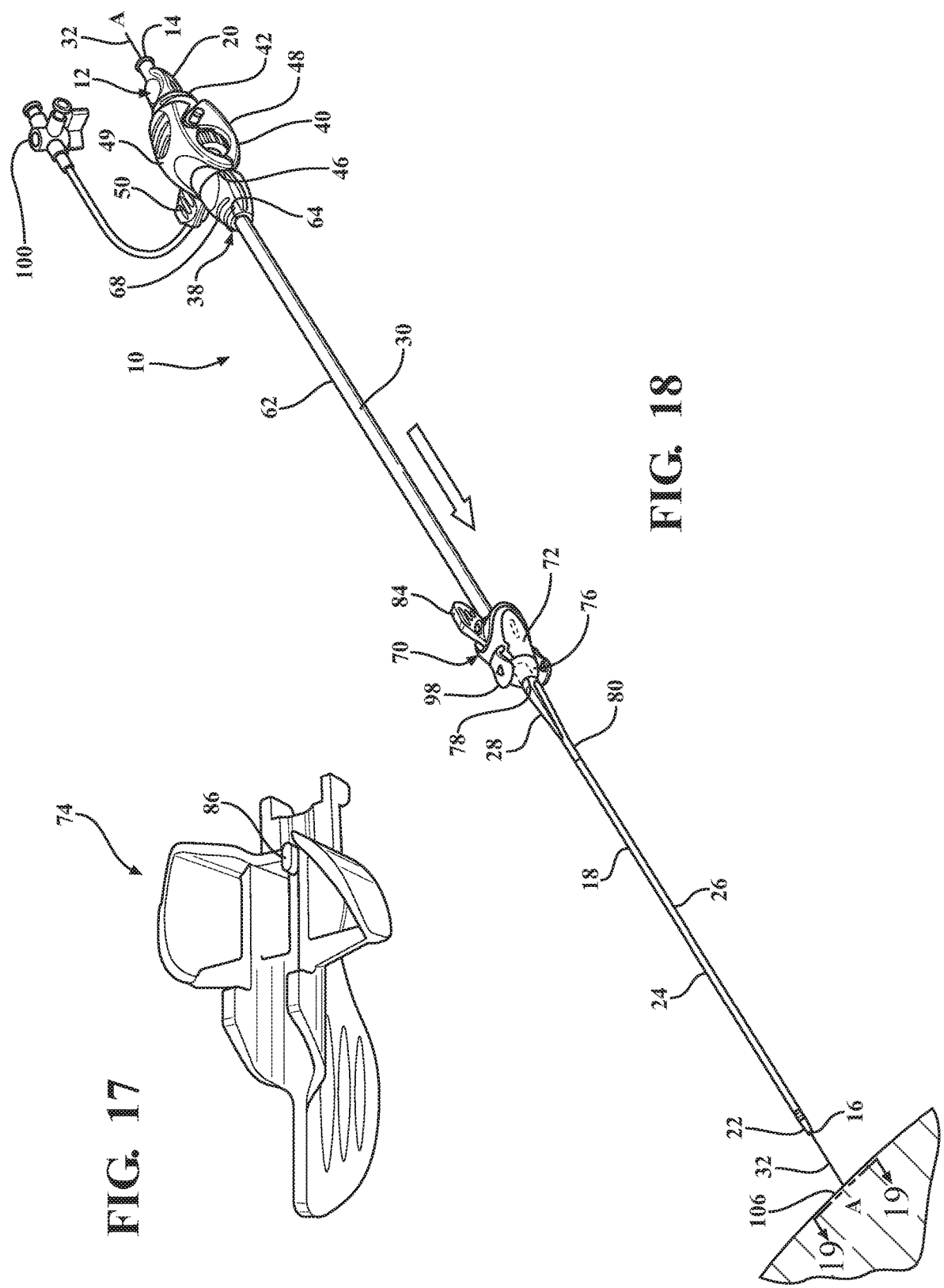

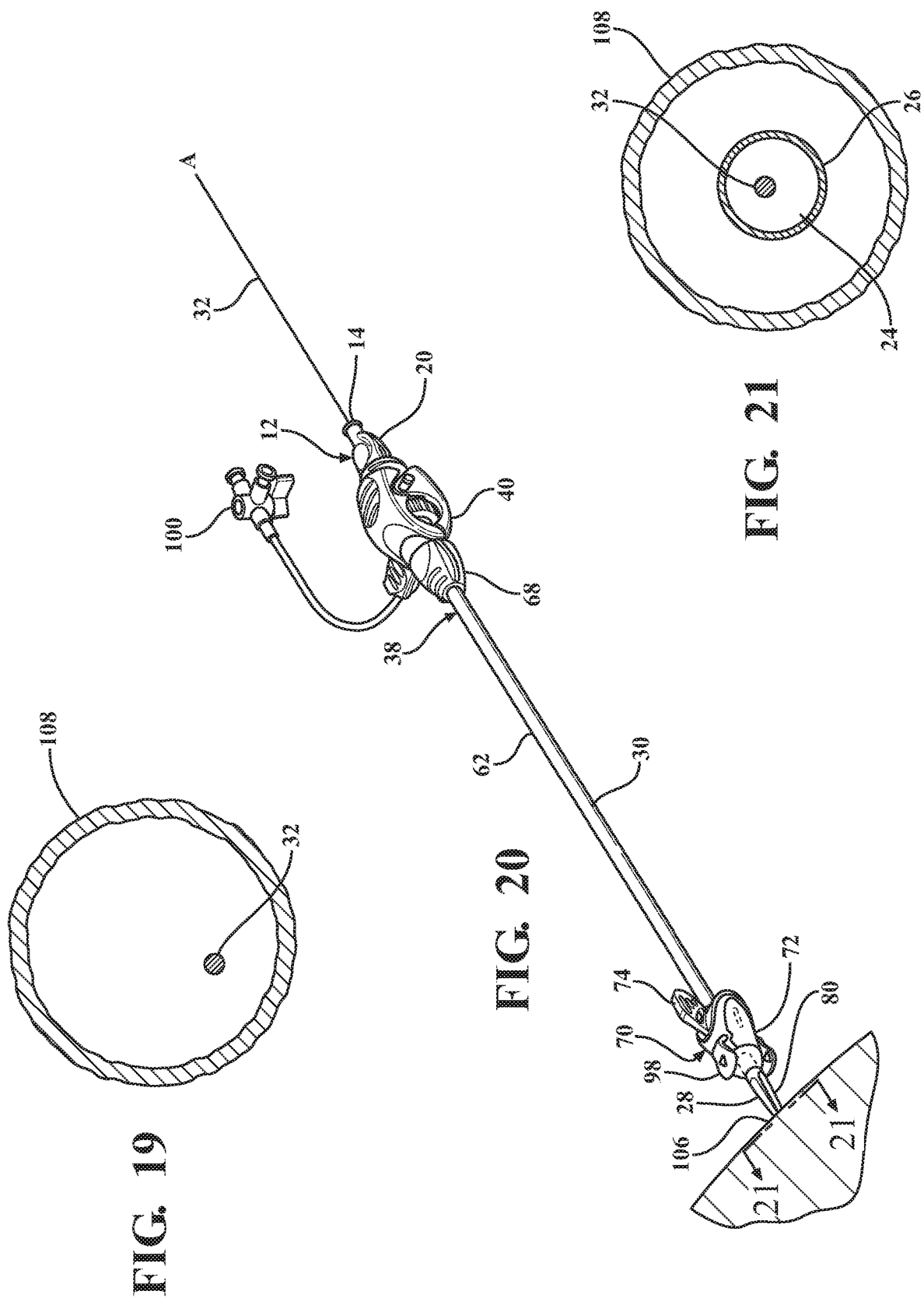

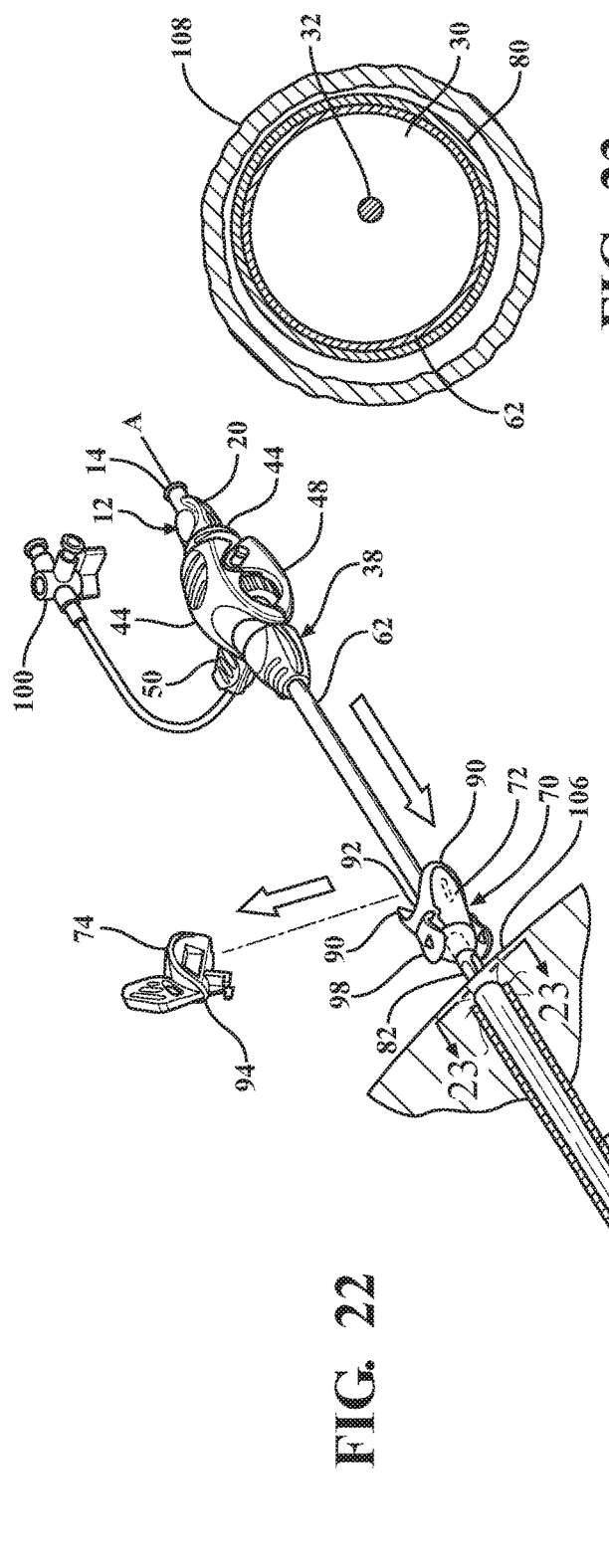
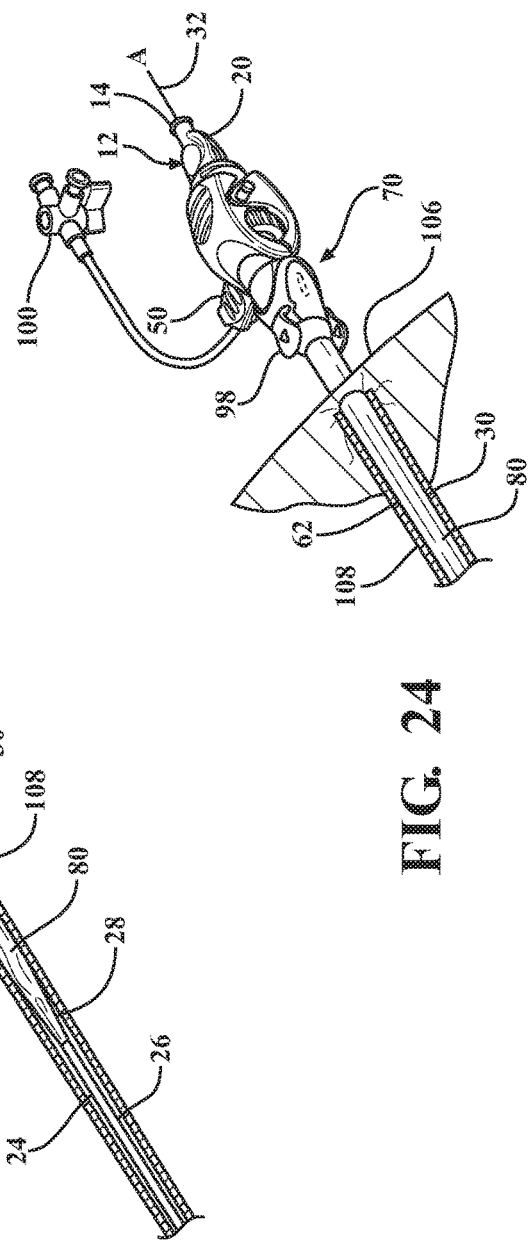
FIG. 22
FIG. 23
FIG. 24

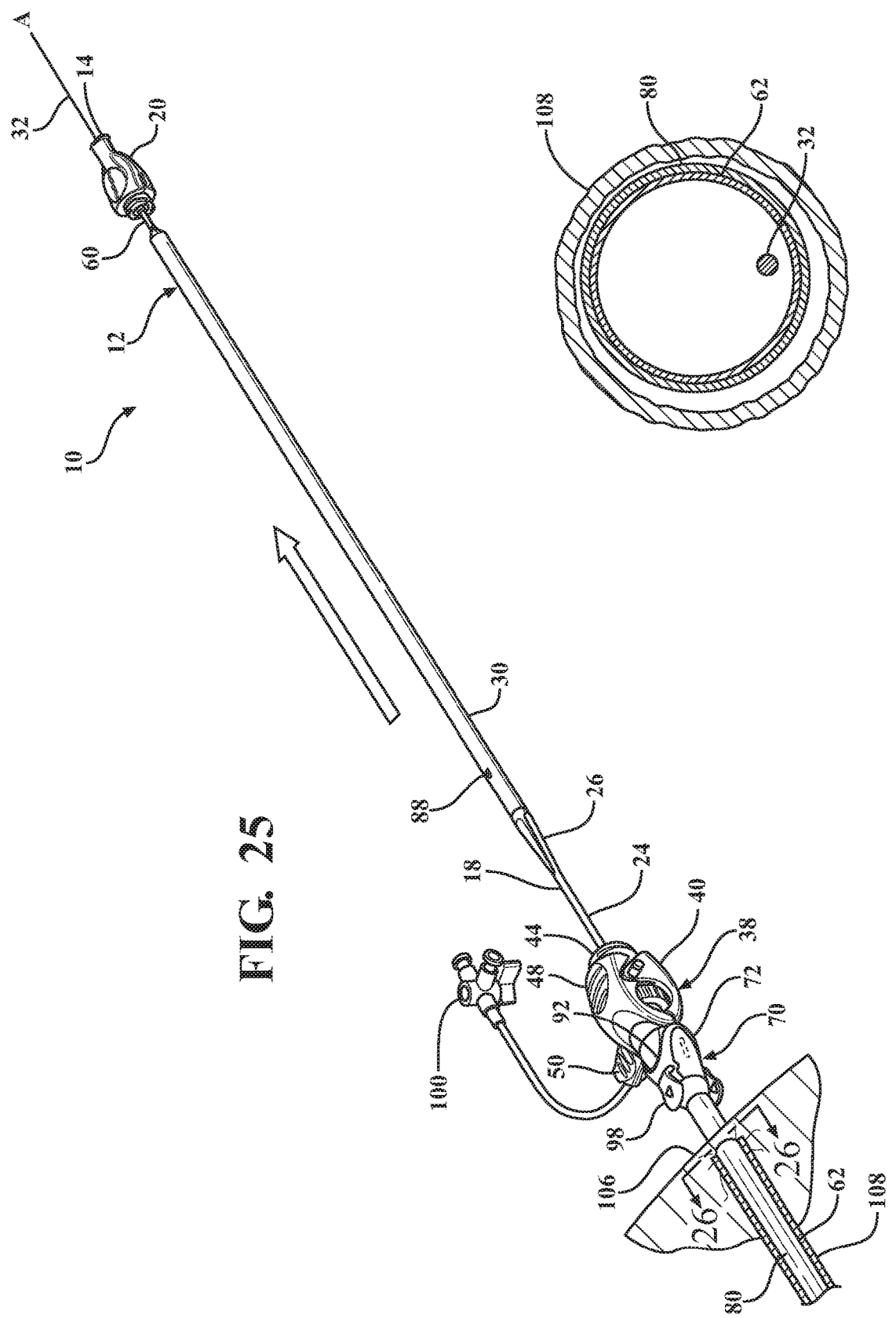

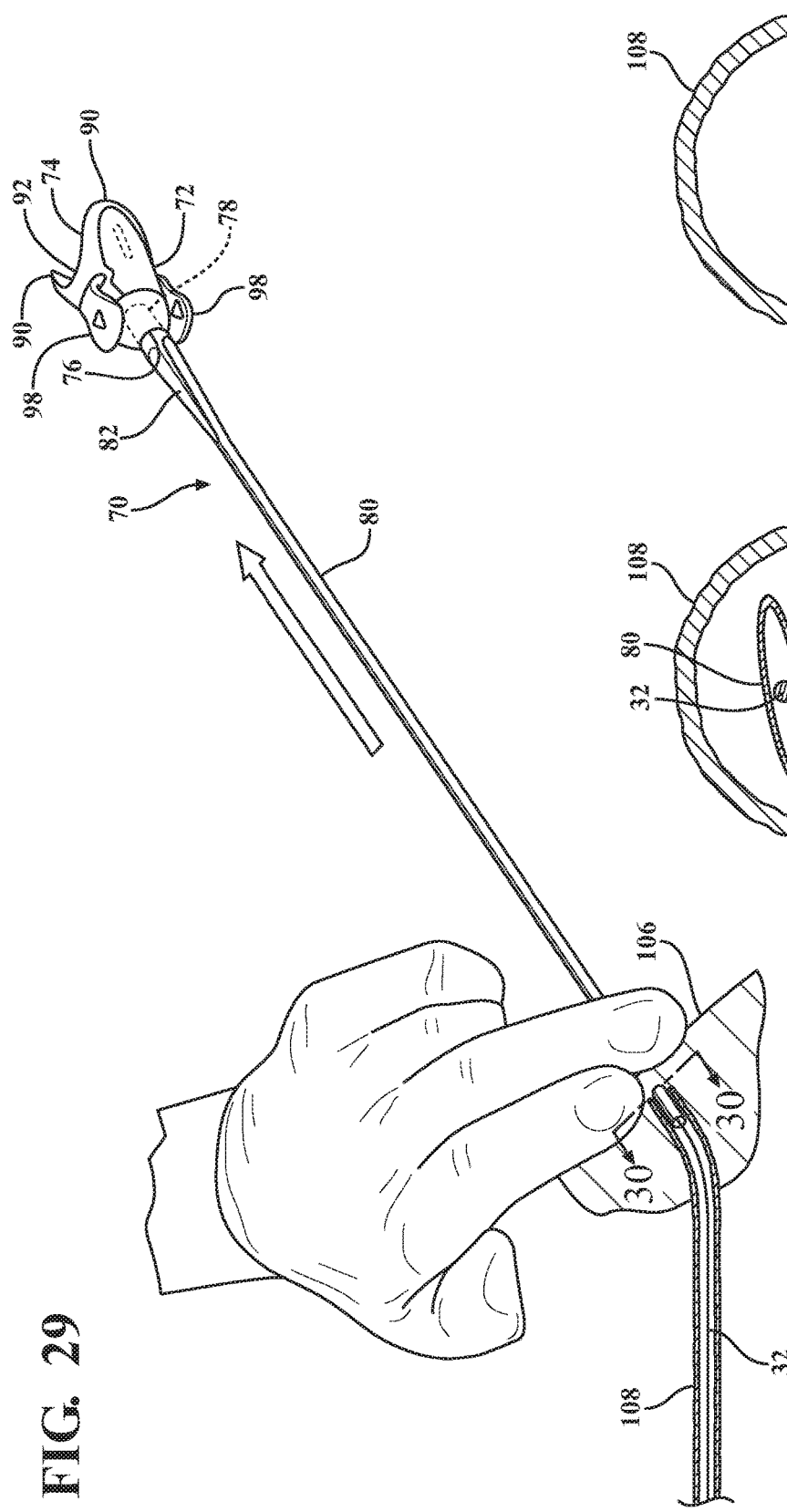
FIG. 29
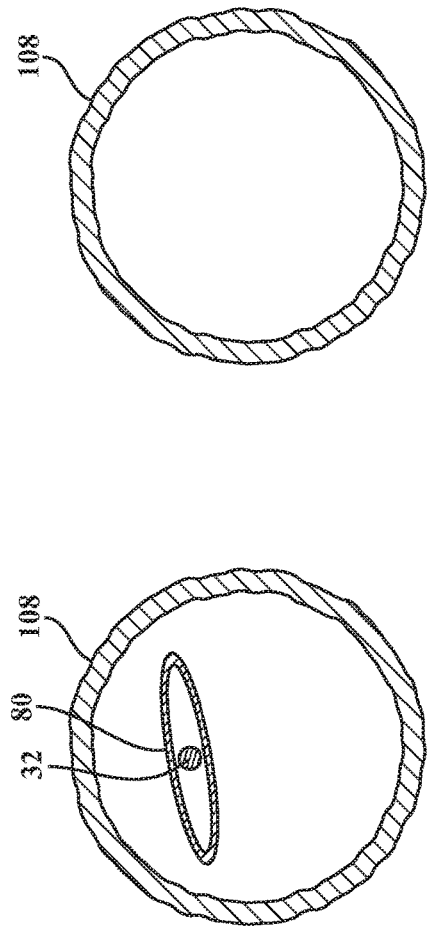
FIG. 30
FIG. 31

EXPANDABLE INTRODUCER ASSEMBLY AND METHOD OF USING SAME

BACKGROUND OF THE INVENTION

1. Field of the Invention

The present disclosure relates generally to medical devices and procedures. In particular, the present disclosure relates to expandable introducer assemblies, and methods of using the same.

2. Description of the Prior Art

This section provides background information related to the present disclosure which is not necessarily prior art.

Numerous procedures have been developed that involve the percutaneous insertion of a medical device into the body of a patient, with the medical device being introduced into the body by a variety of known techniques. For example, access to coronary arteries, carotid arteries, the aorta, and peripheral vessels or other tubular members of the body for percutaneous therapeutic, diagnostic, and guide catheters is often made through introducer sheaths which are positioned into body vessels from outside the bodies. Such access sites include, but are not limited to, the common femoral artery/vein and the radial arteries, as well as the ureter, urethra, intestinal track, veins and other tubular tissues. However, the use of introducer sheaths and/or medical devices which are large relative to the body vessels to which they are inserted poses risks and challenges to both the patient and the physician.

For example, relative to femoral sheaths and catheters, larger introducer sheaths create sizeable arteriotomies in the femoral artery which cause more trauma to the patient, such as through artery avulsion, and create more challenges in placement of the sheath with risk of dissection. In addition, the forces required by the physician to insert the larger introducer sheaths and/or medical devices into the body vessel can be higher than desired and create medical issues for the patient if calcification within the body vessel is dislodged during insertion of the introducer sheath and/or medical device.

Methods of accessing a body vessel with a larger introducer sheath and/or medical device can begin by dilating the vessel with a radially expanding intravascular sheath assembly prior to introducing the medical device. However, such radially expanding sheaths have complex mechanisms, such as ratcheting or balloon mechanisms, that expand and maintain the sheath in an expanded configuration while a medical device with a large diameter is introduced. Further, since the mechanisms effectuate the expansion of the body vessel, they do not provide a user with tactile feedback, and can even pose a risk of dissection during the procedure. Accessing the body vessel remains a challenge with existing expandable sheath assemblies due to the relatively large profile of the medical device inserted which causes longitudinal and radial tearing of the vessel during insertion. As mentioned above, these prior art delivery systems can even dislodge calcified plaque within the vessels during insertion, posing an additional risk of clots caused by the dislodged plague.

Accordingly, there remains a need in the art for an improved expandable introducer assembly for use with the percutaneous insertion of a medical device into a body vessel of a patient.

SUMMARY OF THE DISCLOSURE

This section provides a general summary of the disclosure and is not intended to be a comprehensive disclosure of its full scope, aspects, objectives, and/or all of its features.

An expandable introducer assembly for use in inserting a medical device into a body vessel of a patient includes a dilator subassembly extending from a proximal end to a distal end along an axis. The dilator subassembly includes a dilator having an insertion portion disposed adjacent the distal end, an expansion portion disposed adjacent the distal end, and a tapered transition portion disposed between the insertion and expansion portions and being tapered outwardly from the insertion portion to said expansion portion. The dilator subassembly includes a distal sheath disposed in overlaying and surrounding relationship with the insertion portion of the dilator. An introducer subassembly is disposed in surrounding and coaxial relationship with the expansion portion of the dilator. The introducer subassembly includes a valve disposed adjacent the proximal end and an introducer sheath extending from the valve in overlaying relationship with the expansion portion of the dilator. An expandable sheath subassembly is releasably interlocked with the dilator subassembly and includes an expandable sheath disposed in overlaying relationship with the tapered transition portion of the dilator and in nested relationship between the insertion portion of the dilator and the distal sheath.

The subject disclosure also includes a method of inserting an expandable introducer assembly into a body vessel of a patient. The method begins by inserting an insertion portion of a dilator overlaid with a distal sheath comprised of a low friction polymeric material into a body vessel of a patient. The insertion portion of the dilator inserted into the body vessel also includes an expandable sheath nested between the insertion portion and the distal sheath. The method proceeds by axially advancing the expandable introducer assembly further into the body vessel to radially expand the body vessel with a tapered transition portion of the dilator disposed next adjacent the insertion portion and which is overlaid with the expandable sheath extending outwardly from the distal sheath. The method proceeds by releasing the dilator from an interlocked relationship with the expandable sheath, and then advancing the released dilator further into the body vessel to concurrently axially advance an expansion portion of the dilator overlaid with an introducer sheath through the expandable sheath and into the body vessel. The concurrent axial advancement of the expansion portion of the dilator and the introducer sheath relative to the stationary expandable sheath causes the expandable sheath to retract out from its nested relationship under the distal sheath and into overlaying relationship with the introducer sheath that is axially advanced into the body vessel concurrently with the expansion portion of the dilator.

The subject expandable introducer assembly and method of using same advantageously allows the tapered transition and expansion portions of the dilator which have a larger diameter than a lower insertion profile of the insertion portion of the dilator, to be slidably advanced into the body vessel. The tapered transition portion which is overlaid with an expandable sheath also avoids the need to push the expandable introducer assembly past any calcification that is present within the body vessel, and further provides tactile feedback to a user while inserting the expandable introducer assembly into the body vessel. The subject expandable introducer assembly and method also provides for a smaller profile upon initial insertion of the expandable introducer assembly into a body vessel, followed by a method of expansion that reduces trauma on the patient, including a reduction in the shear, hoop stress/dilation, and axial stress on the body vessel. As a result, the subject expandable introducer assembly and method can even reduce the risk of re-access complications in subsequent treatments.

Further areas of applicability will become apparent from the description provided herein. The description and specific examples in this summary are intended for purposes of illustration only and are not intended to limit the scope of the present disclosure.

BRIEF DESCRIPTION OF THE DRAWINGS

The drawings described herein are for illustrative purposes only of selected embodiments, and are not all possible implementations and thus are not intended to limit the scope of the present disclosure.

FIG. 11 is a magnified and fragmentary perspective view of the expandable sheath subassembly illustrating a crown shaped collar disposed in overlaying relationship with the expandable sheath;

FIG. 12 is a magnified and fragmentary perspective view of the distal end of the dilator subassembly illustrating an expandable sheath nested between the introducer portion of the dilator and a distal sheath;

FIG. 13 is a cross-sectional view of the dilator subassembly taken along 13-13 and illustrating the expandable sheath being pleated and/or folded/wrapped when nested between the introducer portion of the dilator and the distal sheath;

FIG. 14 is a magnified and fragmentary perspective view of the dilator subassembly illustrating a locking orifice defined by the expansion portion of the dilator and the distal sheath overlaying the insertion portion of the dilator;

FIG. 15 is a fragmentary perspective view of the expandable introducer assembly illustrating a locking key disposed in mating relationship with the sheath hub and releasably interlocked with the locking orifice defined by the expansion portion of the dilator;

FIG. 16 is a perspective view of the locking key illustrating a U-shaped stopper for mating with a U-shaped mouth of the sheath hub;

FIG. 17 is a bottom view of the locking key illustrating a locking projection for mating with the locking orifice of the expansion portion of the dilator;

FIG. 18 illustrates an axial movement of the expandable introducer assembly along a guide wire to facilitate an initial insertion of the insertion portion of the dilator through an insertion site of the patient;

FIG. 19 is a cross-sectional view of a body vessel of a patient taken along 19-19 of FIG. 18 illustrating the guide wire extending axially therein;

FIG. 20 illustrates an axial movement of the insertion portion of the dilator into the body vessel to dispose the tapered transition portion of the dilator and the sheath hub next adjacent the insertion site;

FIG. 21 is a cross-sectional view of the body vessel taken along 21-21 of FIG. 20 illustrating the insertion portion of the dilator disposed therein;

FIG. 22 illustrates a removal of the locking key from the sheath hub to allow concurrent axial advancement of the expansion portion of the dilator and the introducer sheath through the sheath hub to advance the dilator subassembly relative to the expandable sheath subassembly and retract the expandable sheath out from its nested relationship between the distal sheath and the insertion portion of the dilator and into overlaying relationship with the introducer sheath axially advanced into the body vessel;

FIG. 23 is a cross-sectional view of the body vessel taken along 23-23 of FIG. 22 illustrating the introducer sheath disposed in overlaying relationship with the expansion portion of the dilator and the expandable sheath disposed in overlaying relationship with the introducer sheath;

FIG. 24 illustrates further concurrent axial advancement of the introducer and dilator subassemblies relative to the expandable sheath subassembly to place the hemostatic valve into abutting and coupled relationship with the hub and dispose the hemostatic valve next adjacent the insertion site;

FIG. 25 illustrates an axial removal of the dilator subassembly from the introducer sheath and the hemostatic valve;

FIG. 26 is a cross-sectional view of the body vessel taken along 26-26 of FIG. 25 illustrating the dilator subassembly removed from the introducer subassembly to leave only the expandable sheath and the introducer sheath within the body vessel;

FIG. 29 illustrates an application of direct radial pressure on the insertion site by a physician to collapse the expandable sheath and maintain hemostasis during removal of the expandable sheath from the body vessel of the patient;

FIG. 30 is a cross-sectional view of the body vessel taken along 30-30 of FIG. 29 illustrating the collapse of the expandable sheath under the influence of the direct radial pressure; and FIG. 31 is a cross-sectional view of the body vessel after removal of the expandable sheath subassembly.

DESCRIPTION OF THE ENABLING EMBODIMENTS

Example embodiments will now be described more fully with reference to the accompanying drawings. The example embodiments are provided so that this disclosure will be thorough and fully convey the scope to those skilled in the art. Numerous specific details are set forth such as examples of specific components, devices, mechanisms, assemblies, and methods to provide a thorough understanding of various embodiments of the present disclosure. It will be apparent to those skilled in the art that specific details need not be employed, that example embodiments may be embodied in many different forms, and that neither should be construed to limit the scope of the disclosure. With this in mind, the present disclosure is generally directed to expandable introducer assemblies of the type used to introduce and withdrawal a medical device (e.g., catheter systems, implants, etc.) into a body vessel of a patient.

Figure 2:
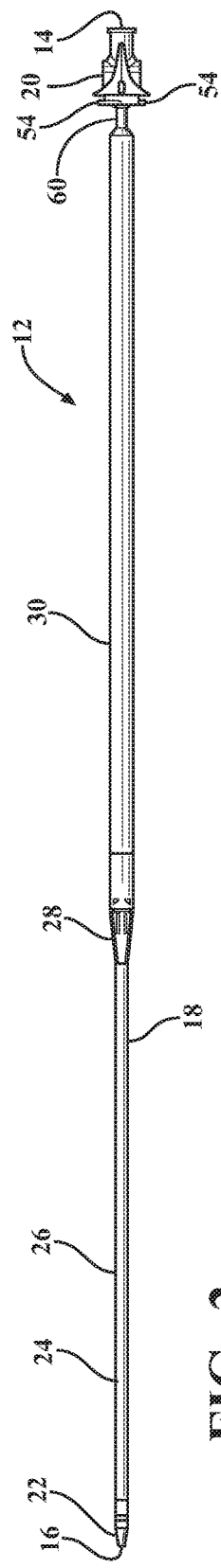
FIG. 2 is a perspective view of a dilator subassembly extending from a proximal end to a distal end and including a dilator having a insertion portion disposed adjacent the distal end, an expansion portion disposed adjacent the proximal end, and a tapered transition portion disposed therebetween and being tapered from the insertion portion to the expansion portion.

Referring to the Figures, wherein like numerals indicate corresponding parts throughout the several views, an expandable introducer assembly 10 for use in inserting a medical device into a body vessel 108 of a patient includes a dilator subassembly 12 which extends from a proximal end 14 to a distal end 16 along an axis A. As best shown in FIG. 2, the dilator subassembly 12 includes a dilator 18 extending from a dilator hub 20 disposed adjacent the proximal end 14 to a distal dilator tip 22 disposed adjacent the distal end 16. The dilator 18 is comprised of a flexible low-friction polymeric material that may be radiopaque and has an insertion portion 24 disposed adjacent the distal end 16 which has a low insertion profile so that, as shown in FIG. 18, an initial insertion of the expandable introducer assembly 10 into the body vessel 108 of the patient can easily be achieved. In a preferred arrangement, the low insertion profile has an insertion outer diameter being approximately 8.5 F. However other suitable outer diameters could be utilized for facilitating an initial insertion of the expandable introducer assembly 10 without departing from the scope of the subject disclosure.

A distal sheath 26 overlays the insertion portion 24 of the dilator 18 and is attached or fused to the distal dilator tip 22. The distal sheath 26 is comprised of low friction polymeric material for creating a low friction surface of the dilator 18 to ease an initial insertion of the dilator 18 into the body vessel 108 of the patient. In a preferred embodiment, the low friction polymeric material is polyethylene, however, other suitable low friction polymeric materials could also be used without departing from the scope of the subject disclosure. As best shown in FIG. 2, the dilator 18 also has a tapered transition portion 28 disposed adjacent the insertion portion 24 and the distal sheath 26. The tapered transition portion 28 is tapered outwardly from the insertion portion 24 to an expansion portion 30 which has an expansion profile being larger than the insertion profile. In a preferred arrangement, the larger expansion profile has an expansion outer diameter being approximately 18 F for compatibility with an appropriately sized introducer device. However, other expansion outer diameters that are larger than the insertion diameters could be utilized without departing from the scope of the subject disclosure. As will be explained in more detail below, and as illustrated by FIGS. 20-22, the tapered and expansion portions 28, 30 of the dilator 18 facilitate a radial expansion of the body vessel 108 during an insertion of the dilator subassembly 12 into the body vessel 108 of the patient. In other words, only radial forces are applied to the vessel wall by the tapered transition portion 28 of the dilator 18. This insertion process is advantageous because it reduces trauma to the body vessel 108 which does not require a pushing of the insertion and tapered transition portions 28, 30 of the dilator 18 past any calcification that is present in the vessel 108, but rather applies radial forces to the vessel wall during insertion of the dilator subassembly 12. Although not expressly shown, the dilator 18 defines a guide wire passageway which extends between the proximal and distal ends 14, 16 and which receives a guide wire 32 for guiding the dilator 18 into the body vessel 108 during insertion. As best illustrated in FIG. 3, the dilator hub 20 defines a guide wire opening 36 for initial receipt of the guide wire 32 to allow the guide wire 32 to be threaded through the dilator 18 along the guide wire passageway.

Figure 1:
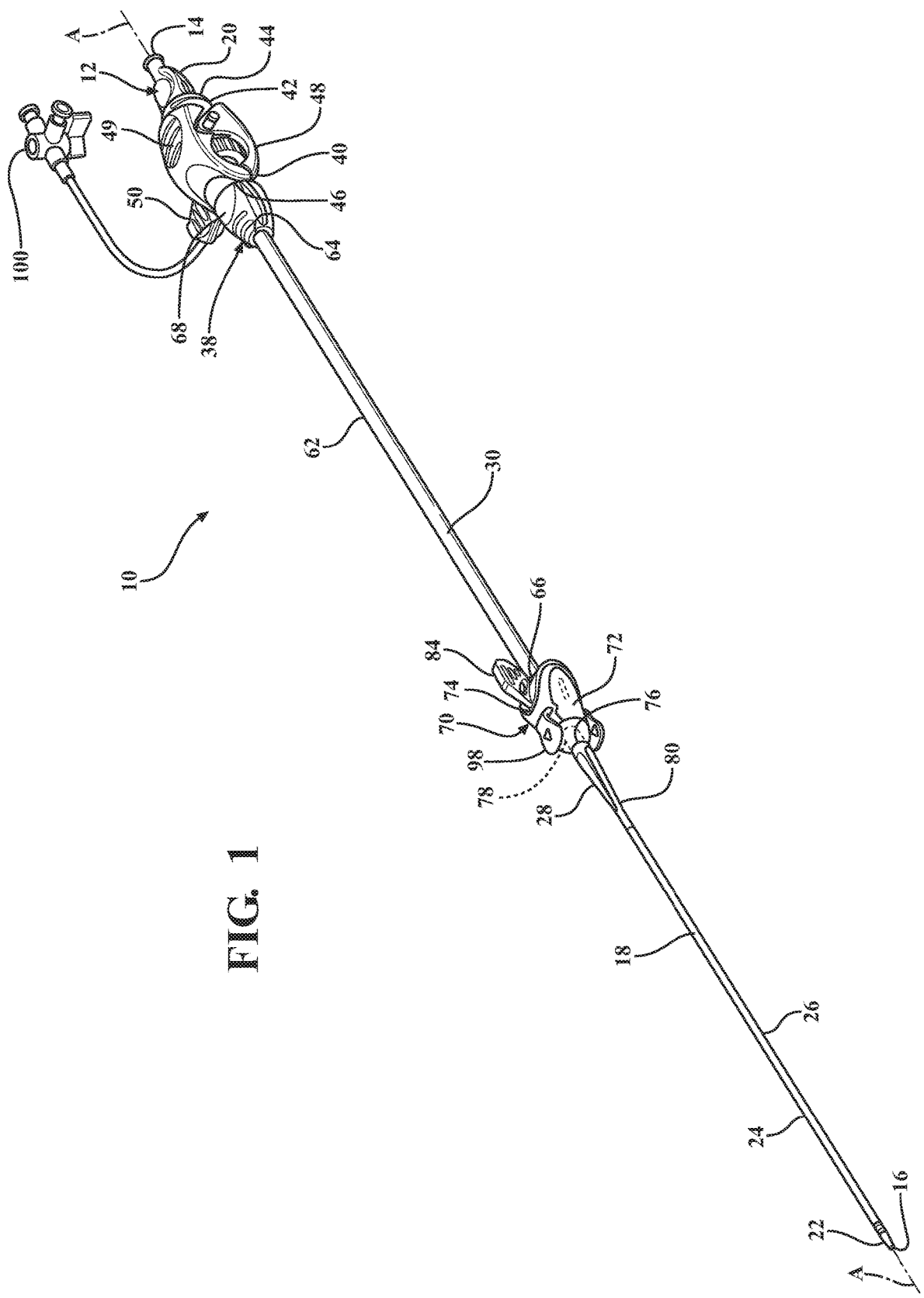
FIG. 1 is a perspective view of an expandable introducer assembly constructed in accordance with the principles of the present disclosure.

As best shown in FIGS. 1 and 18, the expandable introducer assembly 10 includes an introducer subassembly 38 disposed is surrounding and coaxial relationship with the expansion portion 30 of the dilator 18. The introducer subassembly 38 includes a hemostatic valve 40 disposed adjacent a proximal end 14 of the dilator subassembly 12 and releasably interlocked with the dilator hub 20 in a locked condition of the expandable introducer assembly 10. In a preferred embodiment, the hemostatic valve 40 can be a variable diameter seal hemostatic valve as described in co-owned U.S. patent application Ser. No. 14/326,593 entitled "A Medical Valve with a Variable Diameter Seal" or U.S. patent application Ser. No. 14/726,099 entitled "An Automatic Medical Valve with Variable Seal", the entire disclosures of which is incorporated by reference. However, other valves, such as iris valves, laproscopic ports, slit valves, or the like, can also be utilized without departing from the scope of the subject disclosure.

Figure 7:
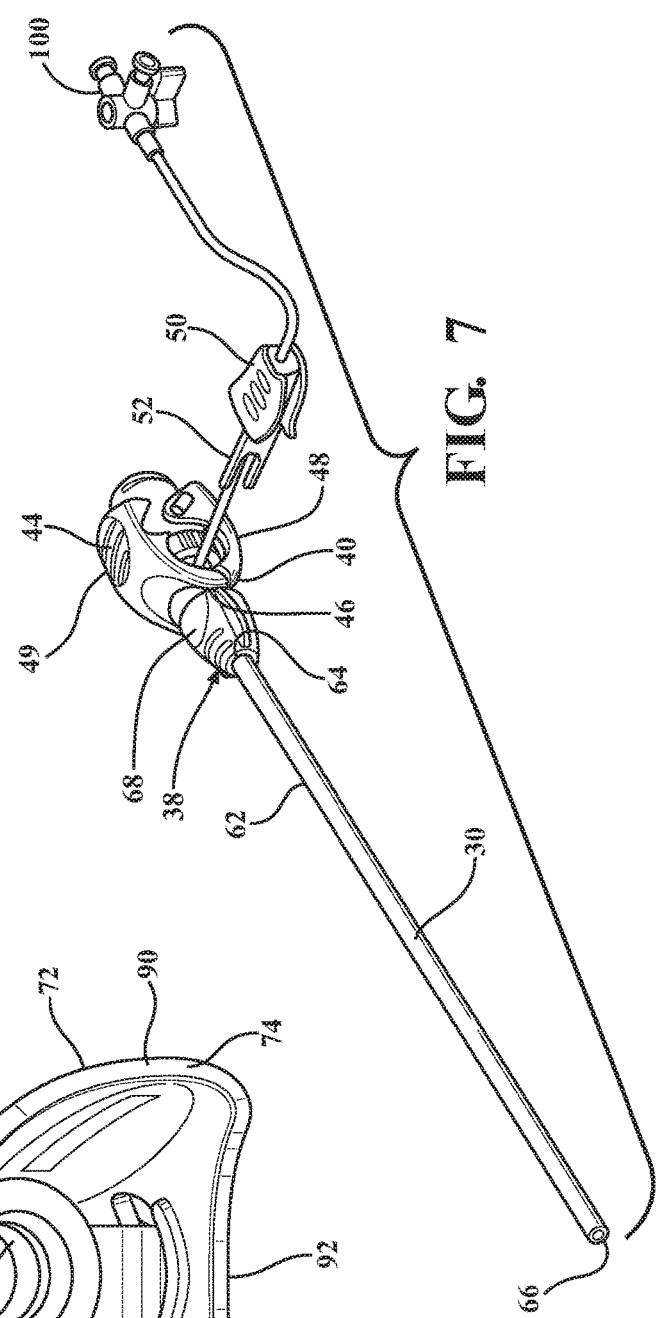
FIG. 7 is a perspective view of an introducer subassembly including an introducer sheath extending from a hemostatic valve.
Figure 9:
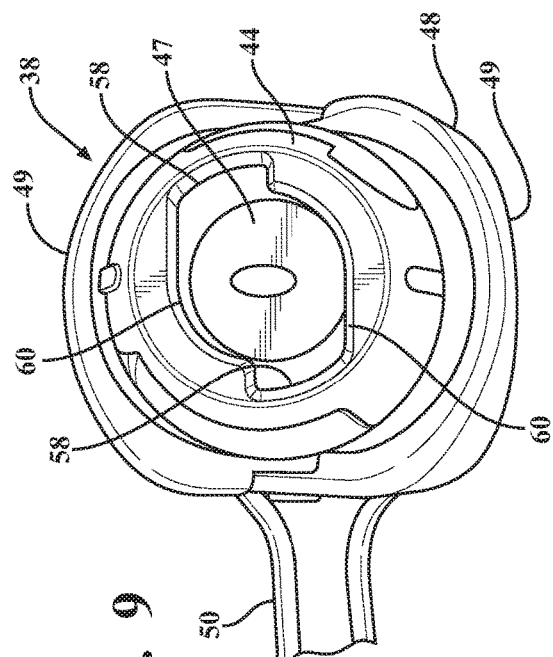
FIG. 9 is an end view of the introducer subassembly illustrating an elastomeric seal compressed within the hemostatic valve and a plurality of circumferential grooves and notches defined by a first valve housing end of the hemostatic valve.

The hemostatic valve 40 includes a valve housing 42 extending from a first valve housing end 44 to a second valve housing end 46. As best illustrated in FIG. 9, an elastomeric seal 47 is compressed within the valve housing 42 and has an inner diameter for use in establishing a seal with a medical device inserted through the first valve housing end 44 of the hemostatic valve 40. A manual actuator 48, such as a pair of lever arms 49 or the like, is interconnected to the valve housing 42 for allowing a physician to interact with the expandable introducer assembly 10 and vary a size of the inner diameter of the elastomeric seal 47 to establish an open condition of the hemostatic valve, such as illustrated in FIG. 9. As best illustrated in FIGS. 1 and 7, a locking member 50 is releasable interconnected with the manual actuator 48 for maintaining the hemostatic valve 40 in the open condition. As will be explained in more detail below, the locking member 50 allows the dilator subassembly 10 to be axially threaded or advanced through the hemostatic valve 40, particularly through the inner diameter of the elastomeric seal 47, to dispose the hemostatic valve 40 in abutting relationship with the dilator hub 20 in the locked position of the expandable introducer assembly 10. The locking member 50 also allows the dilator subassembly 12 to be axially removed from the hemostatic valve 40 once the introducer subassembly 38 is introduced into the body vessel 108 of a patient. In a preferred arrangement, the locking member 50 includes at least one locking pin 52 disposed in engaging relationship with the pair of lever arms 49 to hold the lever arms 49 in a compressed position and maintain the hemostatic valve 40 in the open condition. However, other means of locking and maintaining the hemostatic valve 40 in the open condition could be utilized without departing from the scope of the subject disclosure.

Figure 3:
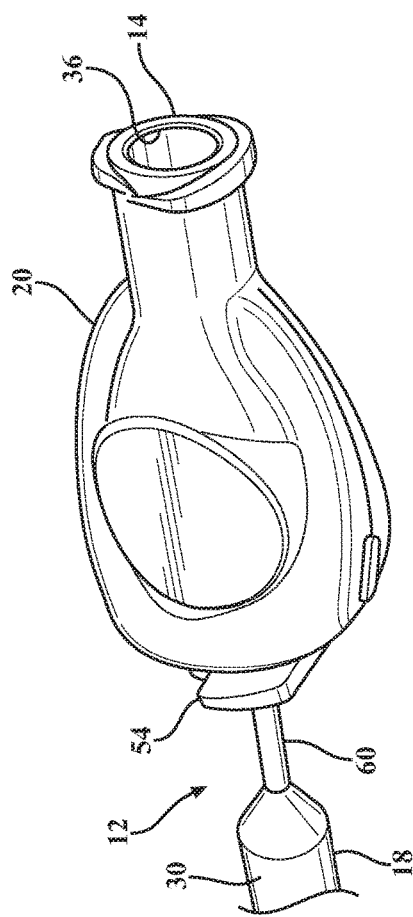
FIG. 3 is a magnified and fragmentary perspective view of the distal end of the dilator subassembly illustrating a dilator hub defining an guide wire opening for receiving a guide wire to guide the expandable introducer assembly into a body vessel of a patient.
Figure 4:
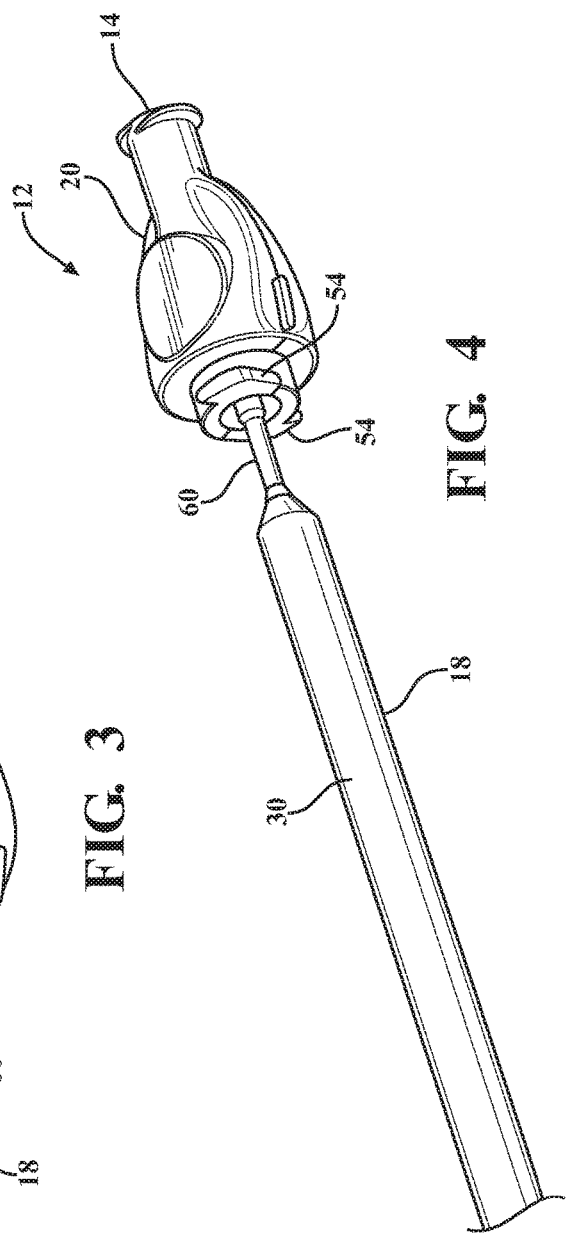
FIG. 4 is a fragmentary perspective view of the proximal end of the dilator subassembly illustrating a guide tube extending between the dilator hub and the expansion portion of the dilator, and a plurality of locking tabs extending from the dilator hub that lock to a proximal end of a valve.
Figure 5:
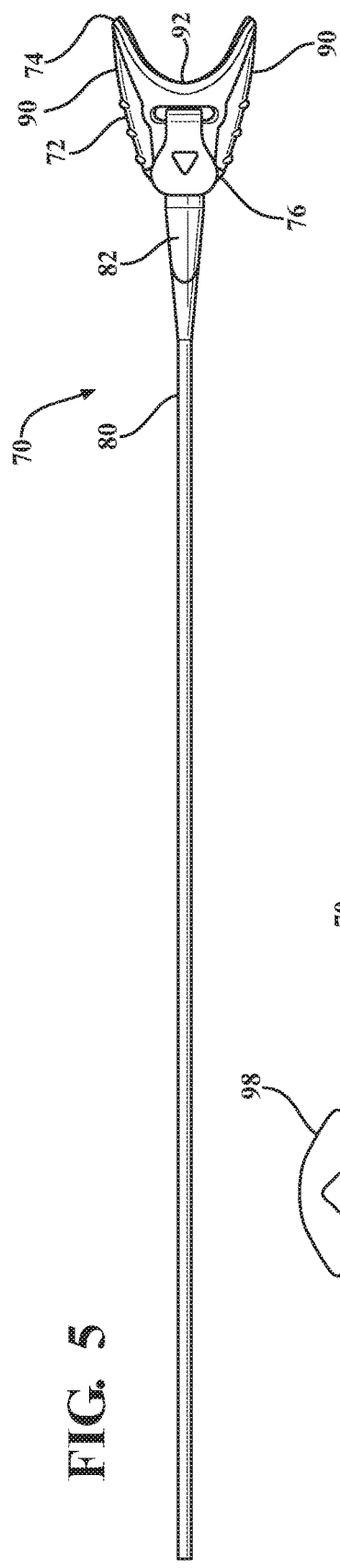
FIG. 5 is a top view of an expandable sheath subassembly including an expandable sheath extending from a sheath hub.

As best illustrated in FIGS. 3-4 and 9, in a preferred arrangement the dilator hub 20 includes a plurality of ramped locking tabs 54 and the first valve housing end 44 defines a plurality of circumferential grooves 56 opening to notches 58 for receiving the ramped locking tabs 54 and allowing manual rotation of the ramped locking tabs 54 within the circumferential grooves 56 to establish the interlocked relationship of the hemostatic valve 40 with the dilator hub 20. Put another way, the dilator hub 20 is rotatable about the axis A to threadingly interlock the hemostatic valve 40 to the dilator hub 20 and establish the locked condition of the expandable introducer assembly 10. As will be described in more detail below, after the dilator and introducer sheath subassembly 12, 38 have been axially advanced into the body vessel and the physician desires to unlock the dilator subassembly 12 from the introducer subassembly 38, the dilator hub 20 is counter-rotated about the axis A to unthread the ramped locking tabs 54 from the circumferential grooves 56 and align the ramped FIG. 54 with the notches 58 to allow the dilator subassembly 12 to be axially retracted from the introducer subassembly 38 through the hemostatic valve 40. Although the interlocked relationship between the dilator hub 20 and the hemostatic valve 40 has been described with respect to ramped locking tabs 54 and circumferential grooves 56/notches 58, other means of establishing the interlocked relationship, such as a direct snap fit or the like, could also be utilized without departing from the scope of the subject disclosure.

As best illustrated in FIGS. 2-4, the dilator subassembly 12 includes a guide tube 60 disposed between the dilator hub 20 and the expansion portion 30 of the dilator 18 for interconnecting the dilator hub 20 with the expansion portion 30 of the dilator 18. The guide tube 60 is disposed in coaxially aligned relationship with the elastomeric seal 47 of the hemostatic valve 40 when the hemostatic valve 40 is interlocked with the dilator hub 20. The guide tube 60 has an outer guide tube diameter being less than the inner diameter of the seal when the hemostatic valve 20 is disposed in the open position to eliminate any radial compression forces imposed on the elastomeric seal 47 by the dilator subassembly 12. Put another way, the guide tube 60 is not radially compressed against the elastomeric seal 47 in the interlocked position of the hemostatic valve 40 and dilator hub 20, but rather is disposed in spaced relationship with the elastomeric seal 47 to reduce stress and wear on the elastomeric seal 47 of the hemostatic valve 40 during shipment and storage of the expandable introducer assembly 40 in the locked and open condition prior to use.

Figure 8:
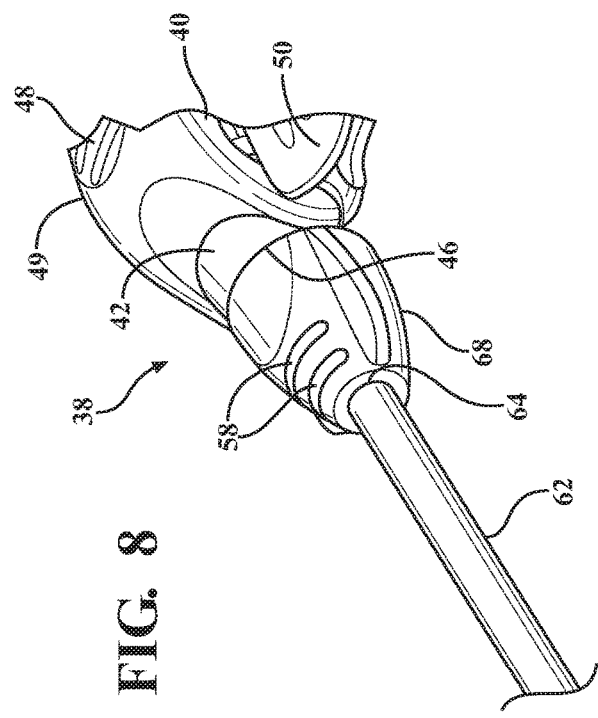
FIG. 8 is a magnified fragmentary view of a portion of FIG. 7 illustrating a nose cap threadingly secured to the hemostatic valve and defining a plurality of recesses.

The introducer subassembly 38 includes a proximal introducer sheath 62 disposed in surrounding and coaxial relationship with the expansion portion 30 of the dilator 18. The proximal introducer sheath 62 extends from a first introducer sheath end 64 being fixed to the second valve housing end 46 of the hemostatic valve 40 to a second introducer sheath end 66 disposed in spaced relationship with the tapered transition portion 28 of the dilator 18. The introducer sheath 62 preferably has a constant introducer sheath diameter extending along its length which is complementarily sized to and disposed in overlaying relationship with the expansion portion 30 of the dilator 18. In a preferred arrangement, the constant diameter ranges between 16 FR to 34 FR and is complementarily sized to the medical device that will be passing through the introducer sheath 62 and into the body vessel 108. However, other constant diameter ranges could also be utilized without departing from the scope of the subject disclosure. The introducer sheath 62 can also be designed and fabricated using known methods such as coextruded tubing or reinforced construction having a PTFE or other low friction polymer liner, reinforced layer and thermoplastic polymer outer jacket. As best illustrated in FIGS. 7 and 8, the hemostatic valve 40 includes a nose cap 68 threadingly secured to the second valve housing end 46 for establishing a compression fit of the introducer sheath 62 between the nose cap 68 and the second valve housing end 40.

As best shown in FIG. 1, the expandable introducer assembly 10 includes an expandable sheath subassembly 70 releasably interlocked with the dilator subassembly 12 in the locked condition of the expandable introducer assembly 10. The expandable sheath subassembly 70 is disposed in surrounding and coaxial relationship with the insertion and tapered transition portions 24, 28 of the dilator 18. The expandable sheath subassembly 70 includes a sheath hub 72 extending from a first hub end 74 releasably interlocked with the expansion portion 30 of the dilator 18 to a second hub end 76 which defines a hub passageway 78 disposed in surrounding and coaxial relationship with the expansion portion 30 of the dilator 18. The expandable sheath assembly 70 includes an expandable sheath 80 extending from the second hub end 76 to adjacent the distal dilator tip 18 of the dilator 18. As best illustrated in FIGS. 10-13, the expandable sheath 80 overlays the tapered transition portion 28 and is nested between the distal sheath 26 and the insertion portion 24 when the expandable introducer assembly 10 is disposed in the locked condition. As further illustrated in FIG. 13, in a preferred embodiment the expandable sheath 80 is pleated, rolled, or folded upon itself when nested between the distal sheath 26 and the insertion portion 24 of the dilator 18.

Figure 10:
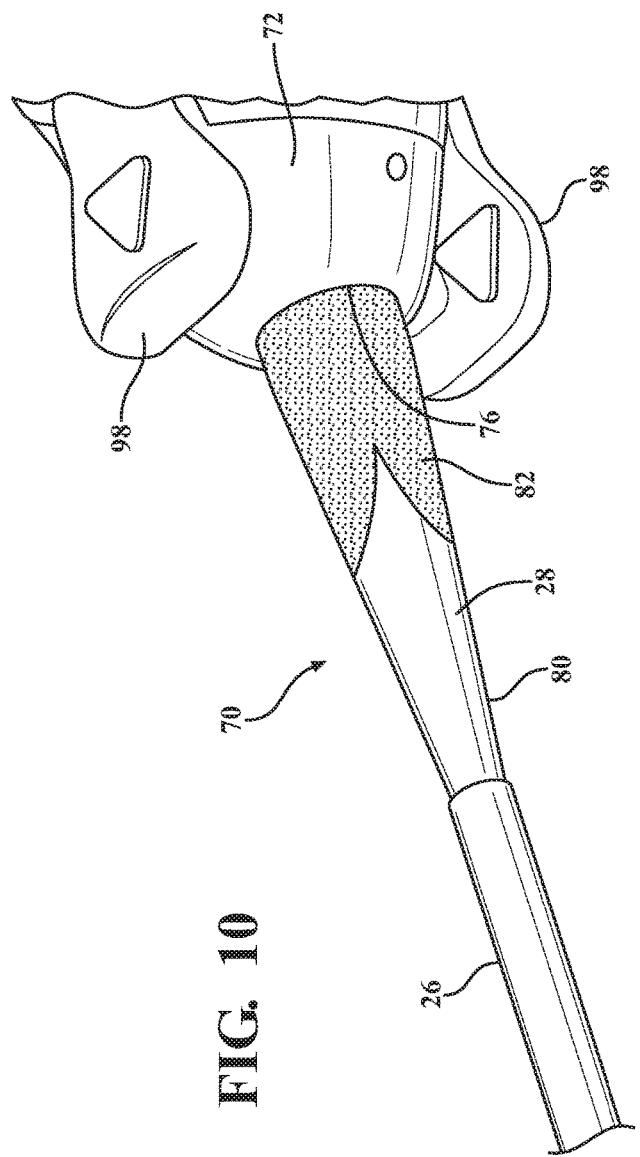
FIG. 10 is a magnified and fragmentary perspective view of the expandable sheath subassembly illustrating a duckbill shaped collar disposed in overlaying relationship with the expandable sheath.
Figures 27, 28:
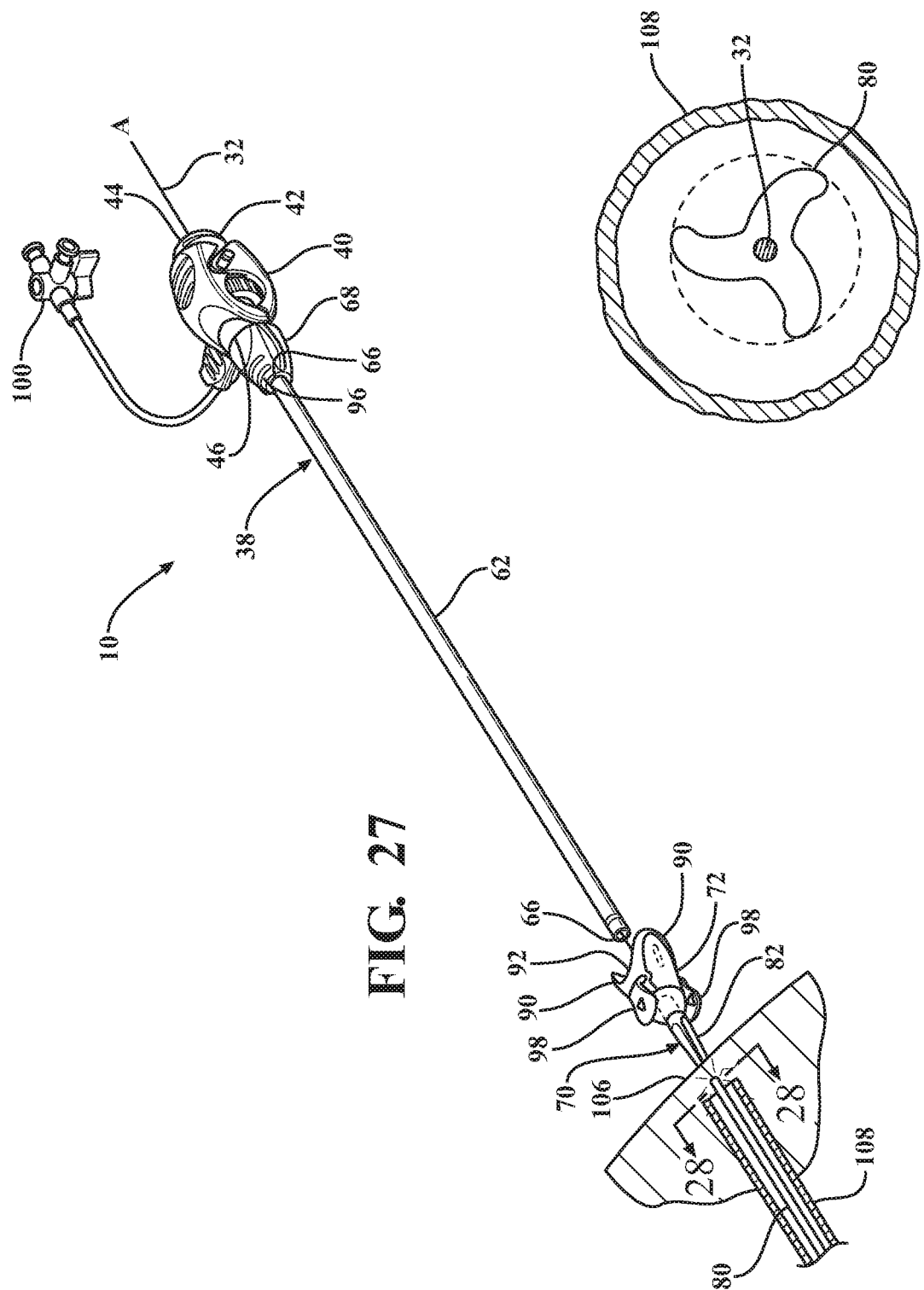
FIG. 27 illustrates an axial removal of the introducer subassembly out of the expandable sheath subassembly to leave only the expandable sleeve within the body vessel.
FIG. 28 is a cross-sectional view of the body vessel taken along 28-28 of FIG. 27 illustrating the expandable sheath collapsed within the body vessel following removal of the introducer sheath.

As best illustrated in FIGS. 10-11, the expandable sheath subassembly 70 includes a collar 82 disposed adjacent the second hub end 76 in overlaying relationship with the expandable sheath 80. In a preferred arrangement, the collar 82 is thermally bonded to the expandable sheath 80 and has a tensile strength being larger than the expandable sheath 80 to provide column strength and added reinforcement to the expandable sheath 80 as the dilator subassembly 12 is advanced into the body vessel 108 of the patient. As will be described in more detail below, and as best illustrated in FIGS. 27 and 29, upon completion of a medical procedure, only the expandable sheath subassembly 70 will remain in the body vessel 108 of the patient. Accordingly, as best illustrated in FIG. 10, in a first arrangement the collar 82 is duckbill shaped for allowing direct radial pressure applied by a physician on the collar 82 to collapse the expandable sheath 80 within the body vessel 108. For example, as best illustrated in FIG. 27, when a physician removes the introducer sheath subassembly 38 from the expandable sheath subassembly 70, the physician can press down on the collar 82 to seal off the lumen, if desired. As best illustrated in FIG. 11, in an alternative arrangement the collar 82 can be crown shaped to also allow the collar 82 to collapse under direct radial pressure by the physician.

As best illustrated in FIG. 15, the expandable sheath subassembly 70 includes a locking key 84 coupled to the sheath hub 72 and releasably interlocked with the expansion portion 30 of the dilator 18. The locking key 84 prevents axial movement of the introducer and dilator subassemblies 12, 38 relative to one another to establish the interlocked relationship between the introducer subassembly 38 and the dilator subassembly 12. As best illustrated in FIGS. 14-15 and 17, in a preferred arrangement the locking key 84 mates with the first hub end 74 and includes a locking projection 86 disposed in mating relationship with a corresponding locking orifice 88 defined by the expansion portion 30 of the dilator 18. The sheath hub 72 includes a pair of flanges 90 disposed about the first hub end 74 to define a U-shaped mouth 92 and the locking key 84 has a corresponding U-shaped stopper 94 for nesting within the mouth 92 of the sheath hub 72. This mating arrangement prevents the dilator subassembly 12 from axially advancing relative to the expandable sheath subassembly 70 in the locked condition of the expandable introducer assembly 10.

Figure 6:
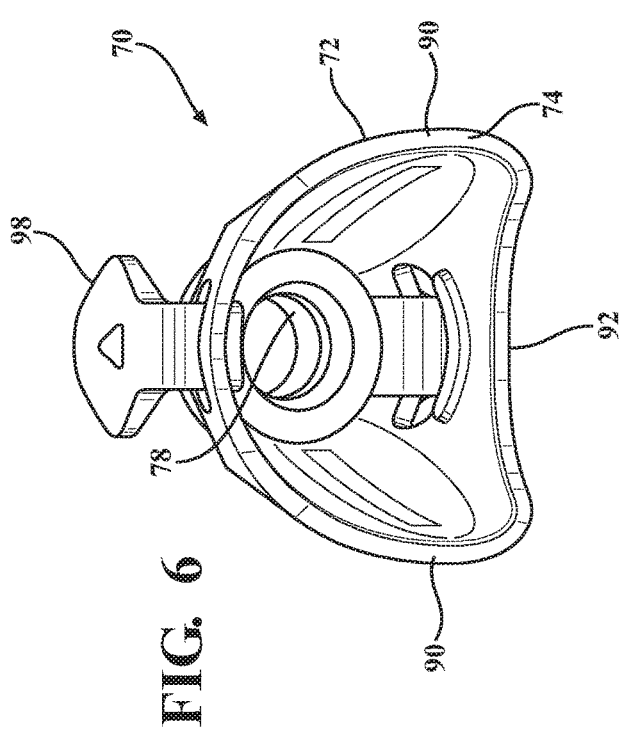
FIG. 6 is an end view of the expandable sheath subassembly illustrating a hub passageway and coupling tabs of the sheath hub.

As best illustrated in FIGS. 20 and 22, after the dilator subassembly 12 is axially advanced into the body vessel 108 to place the sheath hub 72 next adjacent to the insertion site 106, the locking key 74 is removable from the sheath hub 72 and the expansion profile 30 of the dilator 18 to unlock the expandable sheath and dilator subassemblies 12, 70 from one another and establish an unlocked condition of the expandable introducer assembly 10. As best illustrated in FIG. 6, the hub passageway 78 has an inner diameter being slightly larger than the introducer sheath diameter of the introducer sheath 62. As will be described in more detail below, in the unlocked condition of the expandable introducer assembly 10, the dilator and introducer sheath subassemblies 12, 38 can be concurrently axially advanced through the hub passageway 78 to advance the dilator subassembly 12 further into the body vessel and simultaneously pull or retract the expandable sheath 80 out of its nested positioning between the insertion portion 24 of the dilator 18 and distal sheath 26 and into overlaying relationship with the introducer sheath 62. Put another way, the expandable sheath subassembly 70 is held in position with the sheath hub 72 disposed next adjacent the insertion site 106 while the dilator and introducer subassemblies 12, 38 are concurrently axially advanced through the sheath hub 72 and further into the body vessel 108. As best illustrated in FIG. 24, the dilator and introducer subassemblies 12, 38 are concurrently axially advanced until the nose cap 68 of the hemostatic valve 40 is disposed in nested and mating relationship with the U-shaped mouth 92 of the sheath hub 72 to place the expandable sheath 80 in overlaying relationship with the introducer sheath 62. Accordingly, the sliding advancement of the introducer subassembly 38 through the sheath hub 72 by way of concurrent axially advancement with the dilator subassembly 12 retracts the expandable sheath 80 from its nesting positioning and disposes the expandable sheath 80 in overlaying relationship with the introducer sheath 62, and thus provides a protective layer for the introducer sheath 62 when disposed within the body vessel 108. In other words, the expandable sheath provides a protection barrier against shear forces applied to the wall of the body vessel during an introduction of the tapered and expansion portions as well as the introducer sheath. This expandable sheath 80 also provides for easier insertion of the introducer sheath 62 into the body vessel 108 by way of the lower friction barrier that is created by the expandable sheath 80. This insertion process is advantageous because it reduces trauma to the body vessel 108 and does not require a pushing of the introducer sheath 62 past any calcification that is present.

As best illustrated in FIGS. 8 and 15, the nose cap 68 defines a plurality of recesses 96 and the sheath hub 72 includes a plurality of coupling tabs 98 which are each coupled with a respective recess 96 to couple the hemostatic valve 40 to the sheath hub 72. Once the sheath hub 72 and hemostatic valve 40 are coupled together, the entire expandable sheath 80 overlays the introducer sheath 62 to establish one combined sheath disposed within the body vessel 108. Furthermore, once the sheath hub 72 and hemostatic valve 40 are coupled together, and the combined expandable and introducer sheath 62, 80 are disposed in the body vessel 108, the dilator cap 20 is counter-rotated about the axis A to unthread the ramped locking tabs 54 from the circumferential grooves 56 and align the ramped FIG. 54 with the notches 58 to allow the dilator subassembly 12 to be axially retrieved or retracted through the introducer subassembly 38 to leave only the expandable and introducer subassemblies 38, 70 in the body vessel 108 of the patient. In this position, with the hemostatic valve 40 is disposed just outside the insertion site 106 of the patient. As a result, a medical device can now be serially inserted through the hemostatic valve 40 and the introducer sheath 62 and into the body vessel 108 by a physician.

When the use of the medical procedure is complete and the medical device has been removed from the introducer subassembly 38, the coupling tabs 98 of the sheath hub 72 can be radially compressed to release the coupling tabs 98 from the recesses 96 disposed on the nose cap 68 of the hemostatic valve 40. As best illustrated in FIG. 27, the physician is then able to manually pull on the hemostatic valve 40 to retract the introducer sheath 62 along the axis A and out of the expandable sheath 80. This retraction separates the introducer and expandable subassemblies 38, 70 and, as best shown in FIG. 28, leaves the expandable sheath 80 within the body vessel 108 in a collapsed state. For example, the expandable sheath 80 collapses back to approximately less than a 12 F profile to facilitate removal. As described previously, and as shown in FIGS. 29 and 30, direct radial pressure can now be applied by a physician on the collar 82 to collapse the expandable sheath 80 within the body vessel 108 and maintain hemostasis. The expandable sheath 80 can then be slowly removed from the body vessel 108 and appropriate closure procedures can be utilized to close the insertion site 106 of the patient.

A flush port 100 can be in fluid communication with the hemostatic valve 40 for flushing the expandable introducer assembly 10 prior to introducing the distal dilator tip 22 of the dilator 18 into the body vessel 108 of the patient. As best illustrated in FIG. 12, the insertion portion 24 of the dilator 18 defines a flushing hole 102 which is in fluid communication with the flush port 100 via the guide wire passageway for allowing a back flushing of the expandable sheath 80 and the distal sheath 26 prior to use of the expandable introducer assembly 10. The dilator subassembly 12 also includes a radiopaque marker 104 disposed adjacent the distal dilator tip 22 in nested relationship between the distal sheath 26 and the insertion portion 24 of the dilator 18.

Referring to the Figures, wherein like numerals indicate corresponding parts throughout the several views, the subject disclosure also includes a method of inserting an expandable introducer assembly 10 into a body vessel 108 of a patient along a guide wire 32. As best shown in FIG. 18, the method begins by inserting an insertion portion 24 of a dilator 18 that is overlaid with a distal sheath 26 comprised of a low friction polymeric material and includes an expandable sheath 80 nested between the insertion portion 24 and the distal sheath 26 through an insertion site 106 and into the body vessel 108 of a patient. A flush port 100 is in fluid communication with the dilator 18 for flushing the distal sheath 26 and the expandable sheath 80 prior to introducing the insertion portion 24 of the dilator 18 into the body vessel 108 of the patient.

As best shown in FIG. 21, once the insertion portion 24 of the dilator 18 is placed within the body vessel 108, the insertion portion 24 of the dilator 18 occupies a cross section of the vasculature equal in size to an outer diameter of the distal sheath, preferably about 8.5 F. As best shown in FIG. 20, the method proceeds by axially advancing the insertion portion 24 of the dilator 18 further into the body vessel 108 to radially expand the body vessel 108 with a tapered transition portion 28 of the dilator 18 that is overlaid with the expandable sheath 80 to dispose a sheath hub 72 fixed to the expandable sheath 80 and releasable interlocked with an expansion portion 30 of the dilator 18 next adjacent the insertion site 106. As best shown in FIG. 22, the method proceeds by removing a locking key 84 to unlock the sheath hub 72 from the dilator 18 and allow axial movement of the dilator 18 relative to the sheath hub 72 and the interconnected expandable sheath 80.

As best shown in FIG. 22, once the locking key 84 is removed from the expandable introducer assembly 10, the method proceeds by concurrently axially advancing the expansion portion 30 of the dilator 18 and an introducer sheath 62 disposed in surrounding and overlaying relationship with the expansion portion 30 through the sheath hub 72 and into the body vessel 108 to simultaneously retract the expandable sheath 80 out of its nested relationship with the insertion portion 24 of the dilator 18 and distal sheath 26 and into overlaying relationship with the introducer sheath 62 disposed within the body vessel 108. As best illustrated in FIG. 23, the axial advancement of the introducer sheath 62 results in a radial expansion of the body vessel 108 to the outer diameter of the introducer sheath 62, preferably 18 F. In other words, only radial forces are applied to the vessel wall during insertion of the tapered transition portion 28 of the dilator 18. As also illustrated in FIG. 22, a first introducer sheath end 64 of the introducer sheath 62 is fixed to a hemostatic valve 40. In a preferred embodiment, the hemostatic valve 34 can be a variable diameter seal hemostatic valve as disclosed in co-owned U.S. patent application Ser. No. 14/326,593 entitled "A Medical Valve with a Variable Diameter Seal", the entire disclosure of which is incorporated by reference. However, other valves, such as iris valves, laproscopic ports, or the like, can also be utilized without departing from the scope of the subject disclosure.

As best illustrated in FIG. 24, advancement of the introducer sheath 62 into the body vessel 108 also axially advances the hemostatic valve 40 into abutting and coupled relationship with the sheath hub 72 to dispose the hemostatic valve 40 next adjacent the insertion site 106 of the patient. As best illustrated in FIGS. 6 and 8, the hemostatic valve 40 includes a nose cap 68 which defines a plurality of recesses 96 and the sheath hub 72 includes a plurality of coupling tabs 98 which are each coupled with a respective recess 96 to couple the hemostatic valve 40 to the sheath hub 72. Once the sheath hub 72 and the hemostatic valve 40 are coupled together, the entire expandable sheath 80 overlays the introducer sheath 62 to establish one combined sheath disposed within the body vessel 108.

As best illustrated in FIG. 25, the method proceeds by unlocking the dilator 18 from the hemostatic valve 40 and axially removing the dilator 18 from the introducer sheath 62 and the hemostatic valve 40. In a preferred arrangement, the dilator 18 includes a dilator hub 20 that is rotatably interlocked with a first valve housing end 44 of the hemostatic valve 40. For example, as best illustrated in FIG. 4, the dilator hub 20 includes a plurality of ramped locking tabs 54 and the first valve housing end 44 defines a plurality of circumferential grooves 56 opening to notches 58 for receiving the ramped locking tabs 54 and allowing axial rotation of the ramped locking tabs 54 within the circumferential grooves 56 to establish the interlocked relationship of the hemostatic valve 40 with the dilator hub 20. Accordingly, when a physician desires to unlock the dilator 18 from the hemostatic valve 40, the dilator hub 20 is counter-rotated about the axis A to unthread the ramped locking tabs 54 from the circumferential grooves 56 and align the ramped locking tabs 54 with the notches 58 to allow the dilator subassembly 12 to be axially removed from the introducer sheath 62 and through the hemostatic valve 40.

As best illustrated in FIG. 26, the axial removal of the dilator subassembly 12 leaves only the introducer sheath 62 overlaid with the expandable sheath 80 within the body vessel 108 of the patient. Furthermore, in this arrangement, the introducer sheath 62 is interconnected to the hemostatic valve 40 which is disposed outside the body of the patient. As a result, a medical device can now be serially inserted through the hemostatic valve 40 and the introducer sheath 62 and into the body vessel 108 by a physician.

When the medical procedure is complete and the medical device has been removed from the introducer sheath 62, as best illustrated in FIG. 27, the method proceeds by releasing the sheath hub 72 from the hemostatic valve 40 and axially removing the hemostatic valve 40 and the introducer sheath 62 out of the expandable sheath 80. As best illustrated in FIG. 28, this axial movement separates the introducer sheath 62 from the expandable sheath 80 and leaves the expandable sheath 80 within the body vessel 108 in a collapsed state. Accordingly, as best illustrated in FIG. 29, the method proceeds by the application of direct radial pressure on the expandable sheath 80 by a physician to further collapse the expandable sheath 80 within the body vessel 108 and maintain hemostasis during removal of the expandable sheath 80. As best illustrated in FIG. 30, the expandable sheath has a relative flat cross section in its radially collapsed state and thus can be removed from the body vessel as a "limp noodle". As best illustrated in FIGS. 10 and 11, in a preferred arrangement the expandable sheath includes a collar 82 that is thermally bonded to the expandable sheath 80 and is preferably either duckbill shaped or crown-shaped to facilitate an initial collapse of the expandable sheath 80 in response to direct radial pressure by a physician. As best illustrated in FIG. 30, the method concludes by removing the expandable sheath 80 from the body vessel followed by an appropriate closure method to close the insertion site 106 of the patient.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:
1. An expandable introducer assembly for use in inserting a medical device into a body vessel of a patient comprising:

a dilator subassembly extending from a proximal end to a distal end along an axis;

said dilator subassembly including a dilator having an insertion portion disposed adjacent said distal end, an expansion portion disposed adjacent said proximal end, and a tapered transition portion disposed between said insertion and expansion portions and being tapered outwardly from a distal tapered end disposed adjacent said insertion portion to a proximal tapered end disposed adjacent said expansion portion;

said dilator subassembly including a distal sheath disposed in overlaying and surrounding relationship with said insertion portion from said distal tapered end of said tapered transition portion to a distal tip disposed adjacent said distal end of said dilator;

an introducer subassembly disposed in surrounding and coaxial relationship with said expansion portion of said dilator and including a valve releasably interlocked with said dilator subassembly adjacent said proximal end and an introducer sheath extending from said valve in overlaying relationship with said expansion portion of said dilator; and an expandable sheath subassembly releasably interlocked with said dilator subassembly and including an expandable sheath disposed in overlaying relationship with said tapered transition portion of said dilator and in nested relationship between said insertion portion of said dilator and said distal sheath from said distal tapered end of said tapered transition portion to adjacent said distal t of said dilator.

2. The expandable introducer assembly as set forth in claim 1 further comprising:
said proximal end of said dilator subassembly including a dilator hub; and
said valve releasably interlocked with said dilator hub to establish a locked condition of the expandable introducer assembly.

3. The expandable introducer assembly as set forth in claim 2 further comprising:
said dilator hub including a plurality of ramped locking tabs;
said valve extending from a first valve housing end disposed adjacent said proximal end of said dilator subassembly to a second valve housing end;
said first valve housing end defining a plurality of circumferential grooves opening to notches for receiving said plurality of ramped locking tabs and allowing manual rotation of said plurality of ramped locking tabs within said plurality of circumferential grooves to establish the releasably interlocked relationship of said valve with said dilator hub.

4. The expandable introducer assembly as set forth in claim 2 further comprising:
said dilator subassembly including a guide tube extending along said axis between said dilator hub and said expansion portion of said dilator;
said valve including an elastomeric seal disposed in coaxially aligned relationship with said guide tube when said valve and said dilator hub are disposed in the releasably interlocked relationship; and
said guide tube having an outer guide tube diameter being less than an inner diameter of said elastomeric seal in an open condition to eliminate radial compression forces imposed on said elastomeric seal by said dilator subassembly when the expandable introducer assembly is disposed in the locked condition.

5. The expandable introducer assembly as set forth in claim 2 wherein said expandable sheath is pleated when disposed in nested relationship between said insertion portion of said dilator and said distal sheath.

6. The expandable introducer assembly as set forth in claim 2 further comprising:
said expandable sheath subassembly including a sheath hub extending from a first hub end releasable interlocked with said expansion portion of said dilator to a second hub end which defines a hub passageway disposed in surrounding and coaxial relationship with said expansion portion of said dilator; and
said expandable sheath extending from said second hub end to overlay said tapered transition portion and nest between said distal sheath and said insertion portion of said dilator.

7. The expandable introducer assembly as set forth in claim 6, further comprising:
said expandable sheath subassembly including a collar extending from said second hub end in overlaying relationship with said expandable sheath for providing column strength and added reinforcement to the expandable sheath as said tapered transition portion of said dilator is axially advanced into the body vessel of the patient.

8. The expandable introducer assembly as set forth in claim 7 wherein said collar is duckbill shaped.

9. The expandable introducer assembly as set forth in claim 7 wherein said collar is crown shaped.

10. The expandable introducer assembly as set forth in claim 6 further comprising:
a locking key disposed in mating with said first hub end of said sheath hub and releasably interlocked with said expansion portion of said dilator for preventing axial movement of said dilator and expandable sheath subassemblies relative to one another in the locked condition of the expandable introducer assembly.

11. The expandable introducer assembly as set forth in claim 10 further comprising:
said sheath hub including a pair of flanges disposed about the first hub end to define a u-shaped mouth;
said expansion portion of said dilator defining a locking orifice; and
said locking key defining a stopper disposed in nesting relationship with said u-shaped mouth of said sheath hub and a locking projection disposed in mating relationship with said locking orifice of said expansion portion of said dilator to establish said axially interlocked relationship between said dilator and expandable sheath subassemblies.

12. An expandable introducer assembly for use in inserting a medical device into a body vessel of a patient comprising:
a dilator subassembly extending from a proximal end to a distal end along an axis;
said dilator subassembly including a dilator having an insertion portion disposed adjacent said distal end, an expansion portion disposed adjacent said distal end, and a tapered transition portion disposed between said insertion and expansion portions and being tapered outwardly from said insertion portion to said expansion portion;
said dilator subassembly including a distal sheath disposed in overlaying and surrounding relationship with said insertion portion of said dilator;
an introducer subassembly disposed in surrounding and coaxial relationship with said expansion portion of said dilator and including a valve disposed adjacent said proximal end and an introducer sheath extending from said valve in overlaying relationship with said expansion portion of said dilator;

an expandable sheath subassembly releasably interlocked with said dilator subassembly and including an expandable sheath disposed in overlaying relationship with said tapered transition portion of said dilator and in nested relationship between said insertion portion of said dilator and said distal sheath;

said dilator subassembly including a dilator hub disposed adjacent said proximal end;

said valve releasably interlocked with said dilator hub to establish a locked condition of the expandable introducer assembly;

said dilator subassembly including a guide tube extending along said axis between said dilator hub and said expansion portion of said dilator;

said valve including an elastomeric seal disposed in coaxially aligned relationship with said guide tube when the expandable introducer assembly is disposed in the locked condition; and said guide tube having an outer guide tube diameter being less than an inner diameter of said elastomeric seal in an open condition to eliminate radial compression forces imposed on said elastomeric seal by said dilator subassembly when the expandable introducer assembly is disposed in the locked condition.

13. The expandable introducer assembly as set forth in claim 12 further comprising:
said dilator hub including a plurality of ramped locking tabs;
said valve extending from a first valve housing end disposed adjacent said proximal end of said dilator subassembly to a second valve housing end;
said first valve housing end defining a plurality of circumferential grooves opening to notches for receiving said plurality of ramped locking tabs and allowing manual rotation of said plurality of ramped locking tabs within said plurality of circumferential grooves to establish the releasably interlocked relationship of said valve with said dilator hub.

14. The expandable introducer assembly as set forth in claim 12 wherein said expandable sheath is pleated when disposed in nested relationship between said insertion portion of said dilator and said distal sheath.

15. The expandable introducer assembly as set forth in claim 12 further comprising:
said expandable sheath subassembly including a sheath hub extending from a first hub end releasable interlocked with said expansion portion of said dilator to a second hub end which defines a hub passageway disposed in surrounding and coaxial relationship with said expansion portion of said dilator; and
said expandable sheath extending from said second hub end to overlay said tapered transition portion and nest between said distal sheath and said insertion portion of said dilator.

16. The expandable introducer assembly as set forth in claim 15, further comprising:
said expandable sheath subassembly including a collar extending from said second hub end in overlaying relationship with said expandable sheath for providing column strength and added reinforcement to the expandable sheath as said tapered transition portion of said dilator is axially advanced into the body vessel of the patient.

17. The expandable introducer assembly as set forth in claim 16 wherein said collar is duckbill shaped.

18. The expandable introducer assembly as set forth in claim 16 wherein said collar is crown shaped.

19. The expandable introducer assembly as set forth in claim 15 further comprising:
a locking key disposed in mating with said first hub end of said sheath hub and releasably interlocked with said expansion portion of said dilator for preventing axial movement of said dilator and expandable sheath subassemblies relative to one another in the locked condition of the expandable introducer assembly.

20. The expandable introducer assembly as set forth in claim 19 further comprising:
said sheath hub including a pair of flanges disposed about the first hub end to define a u-shaped mouth;
said expansion portion of said dilator defining a locking orifice; and
said locking key defining a stopper disposed in nesting relationship with said u-shaped mouth of said sheath hub and a locking projection disposed in mating relationship with said locking orifice of said expansion portion of said dilator to establish said axially interlocked relationship between said dilator and expandable sheath subassemblies.

* * * * *